US012660999B2

(12) United States Patent
    Palzer

(10) Patent No.: US 12,660,999 B2
(45) Date of Patent: Jun. 23, 2026

(54) METHOD FOR DETERMINING THE POSITION OF A FLAP CUT ON A CORNEA AND OF THE HINGE BELONGING TO THE FLAP, AND DEVICE FOR CARRYING OUT A METHOD OF THIS TYPE

(71) Applicant: PRECITEC OPTRONIK GMBH, Neu-Isenburg (DE)

(72) Inventor: Gabriel Palzer, Rodgau (DE)

(73) Assignee: PRECITE OPTRONIK GMBH, Neu-Isenburg (DE)

( * ) Notice: Subject to any disclaimer, the term of this patent is extended or adjusted under 35 U.S.C. 154(b) by 652 days.

(21) Appl. No.: 17/917,885

(22) PCT Filed: Mar. 23, 2021

(86) PCT No.: PCT/EP2021/057495
    § 371 (c)(1),
    (2) Date: Oct. 7, 2022

(87) PCT Pub. No.: WO2021/204540
    PCT Pub. Date: Oct. 14, 2021

(65) Prior Publication Data
    US 2023/0148378 A1      May 11, 2023

(30) Foreign Application Priority Data
    Apr. 9, 2020    (DE) ...................... 10 2020 110 041.8

(51) Int. Cl.
    *A61B 3/00*        (2006.01)
    *A61B 3/10*        (2006.01)
    *G06T 7/00*        (2017.01)
(52) U.S. Cl.
    CPC .............. *A61B 3/0008* (2013.01); *A61B 3/10* (2013.01); *G06T 7/0012* (2013.01); *G06T 2207/30041* (2013.01)

(58) Field of Classification Search
    CPC ......... A61B 3/0008; A61B 3/10; A61B 3/113; G06T 7/0012; G06T 2207/30041; A61F 2009/00872; A61F 9/00836
    See application file for complete search history.

(56) References Cited

U.S. PATENT DOCUMENTS 8,858,540 B2    10/2014  Bischoff et al.
9,918,633 B2     3/2018  Lipari
            (Continued)

FOREIGN PATENT DOCUMENTS

DE        102010012616 A1 *  9/2011   ............. A61F 9/008
EP             2729099 B1 * 11/2019   ............. A61B 34/20
            (Continued)

OTHER PUBLICATIONS

Ingawale, A.R.D. et al, A virtual model to assess maximum treatable area in Lasik and feasibility of a temporal hinge; Int Ophthalmol; vol. 38, pp. 2627-2633; 2018; https://doi.org/10.1007/s10792-017-0729-6.
            (Continued)

*Primary Examiner* — Mekonen T Bekele
(74) *Attorney, Agent, or Firm* — Lempia Summerfield Katz LLC

(57)                ABSTRACT
A method and device are disclosed for determining the position of a flap incision on a cornea and the position of the hinge associated with the flap. The method comprises the steps of: capturing an image of an eye, including at least the pupil and the limbus; determining a region including the outer circumference of the flap incision; determining the position of the flap incision; determining a straight region including the hinge; and determining the position of the hinge.

9 Claims, 6 Drawing Sheets

(56)     References Cited

U.S. PATENT DOCUMENTS

| | | | |
|---|---|---|---|
| 10,779,989 B2 | 9/2020 | Donitzky et al. | |
| 2010/0231855 A1* | 9/2010 | Thompson | G06V 40/193 |
| | | | 702/19 |
| 2013/0072916 A1 | 3/2013 | Bischoff et al. | |
| 2014/0135747 A1* | 5/2014 | Donitzky | A61B 34/20 |
| | | | 606/4 |
| 2015/0005752 A1 | 1/2015 | Bischoff et al. | |
| 2016/0183787 A1 | 6/2016 | Lipari | |

FOREIGN PATENT DOCUMENTS

| | | | |
|---|---|---|---|
| WO | 2013004255 A1 | 1/2013 | |
| WO | 2015011692 A1 | 1/2015 | |

OTHER PUBLICATIONS

International Search Report and Written Opinion cited in corresponding international application No. PCT/EP2021/057495; Jun. 18, 2021; 13pp.

* cited by examiner

100

11   19   102   104   25   27

METHOD FOR DETERMINING THE POSITION OF A FLAP CUT ON A CORNEA AND OF THE HINGE BELONGING TO THE FLAP, AND DEVICE FOR CARRYING OUT A METHOD OF THIS TYPE

RELATED APPLICATION DATA

This application is a U.S. national stage of and claims priority to prior filed international application no. PCT/EP2021/057495 filed Mar. 21, 2021 and which claims priority to a German national application no. 10 2020 110 041.8 filed Apr. 9, 2020. The entire contents of these prior filed applications are hereby incorporated by reference herein.

BACKGROUND

1. Field of the Disclosure

The present disclosure relates to a method for determining the position of a flap incision on a cornea and of the hinge associated with the flap, and to a device for carrying out a method of this type.

2. Description of the State of the Art

In refractive surgery of the eye, the overall refractive power of the eye is to be changed in s such a way that conventional corrective devices, such as spectacles or contact lenses, can be dispensed with thereafter. Among various intervention techniques, the lamellar methods, and among those, in particular, the LASIK method ("Laser in situ Keratomileusis") have been established as widely-used methods. To achieve the desired change in the curvature of the cornea, tissue is removed from the inside of the cornea.

Access to the tissue to be ablated is enabled by an incision in the cornea. To do this, a cornea lamella, which comprises the external epithelial layer and the underlying Bowman's membrane are detached by an approximately circular to slightly elliptical incision not quite closed in its circumference. Since the incision on the cornea is not quite closed along its circumference, the lamella, then referred to as a "flap", remains attached to the cornea and can be folded back to one side. The underlying stroma is then exposed to be treated with the laser to create the desired reshaping.

After treatment, the flap can be folded back into place, covering the stroma again. The diameter of the flap is chosen such that it comprises the optical zone of the cornea and is usually about 8 mm-9.5 mm in diameter. The thickness of the lamella is about 90-160 μm.

The position at which the flap remains attached to the cornea, is called a "hinge". The position of the hinge is usually chosen to be superior, i. e., at the top, or nasal. Depending on the choice of the position of the hinge, the position at which the folded-back flap comes to lie during the subsequent laser ablation also changes.

Since it remains common to create the flap by means of a microkeratoma or by means of a laser different from the ablation laser used for reshaping the stroma surface, the ablation laser is ignorant of the position of the hinge or the flap. To avoid damaging the hinge and the flap during the ablation process, the hinge and the flap are usually covered by a material impenetrable to the ablation laser. This can be, for example, a sponge or a metal spatula.

This approach has several drawbacks: additional instruments come into contact with the eye unnecessarily, and the risk of infection is increased. The surgeon can be imprecise in their work when covering the flap, or the eye moves relative to the cover during the procedure. This can lead to the flap being undesirably ablated if it is insufficiently covered, which can disadvantageously affect the ultimate visus. When too much of the flap is covered, part of the otherwise exposed stroma is undesirably covered and is not reached by the ablation treatment. This can also disadvantageously affect the ultimate visus.

SUMMARY

It is an object of the present disclosure to avoid or at least mitigate the above-mentioned drawbacks. In particular, it would be desirable if the protection of the hinge and of the flap would not require the surgeon's attention and thus could be carried out in an easily reproducible manner.

The object is achieved by a method according to the independent method claim.

The method according to the present disclosure serves to determine the position of a flap incision on a cornea and of the hinge associated with the flap and comprises the steps of: capturing an image of a cornea, the image at least comprising the limbus; determining a region comprising the outer circumference of the flap incision and determining the position of the flap incision; or/and determining a straight region comprising the hinge and determining the position of the hinge. Thus, either only the position of the flap incision, only the position of the hinge or both the position of the flap incision and the position of the hinge can be determined.

By capturing one or more images, digital images for example, the image contents can be processed. This usually requires a lot of computing power and can therefore not take place at the required speed, with which the position of the eye can change. Therefore, according to the present disclosure, the outer circumference of the flap incision is first determined within the captured image. The computationally demanding further processing of the digital image data can subsequently be carried out based on the determined circumference. This enables a substantial reduction of the data to be processed and thus a substantial increase in speed.

In accordance with one embodiment, when a plurality of images is captured, the captured images can be averaged. Alternatively, or additionally, when there is a plurality of images, a change in the reflexes on the edges of the incision from one image to another can be considered.

In an embodiment of the present disclosure, it is provided that the step of determining a region including the outer circumference of the flap comprises determining an approximately circular or annular region as the region including the outer circumference of the flap incision. This is based on the assumption that the flap incision is essentially circular.

When determining the position of the flap incision, or the position of the outer circumference of the flap incision, a circular or annular region can thus already be assumed. It may be preferred, in particular, to assume neither a circle nor an ellipse for the region including the outer circumference of the flap incision, but a learned-in, specific approximately circular shape. This substantially reduces the number of image regions to be considered and thus substantially increases the processing speed.

In a further development of the inventive idea, the step of determining a straight region including the hinge comprises limiting the possible position of the straight region to a region within the circular region. The hinge—thus the region of the cornea in which the flap is moveably attached to the rest of the cornea—can only be situated within the already determined circular region. Limiting the possible position of the hinge to a region within the already found circular incision region in turn reduces the amount of data to be processed and increases the processing speed.

In an embodiment, it can be provided that the step of determining the position of the hinge comprises comparing the currently determined position to the previous position of the hinge. Once the position of the hinge has been determined, when the position of the hinge is determined again at an immediately following point in time, this position to be newly found can only be situated within a determined region which extends around the previous position of the hinge. In other words, the position of the hinge cannot change in an abrupt fashion.

In particular, when determining the position of the hinge, the time can be considered which has elapsed between the previous position and the currently determined position of the hinge. Depending on the time period between the position of the hinge currently to be determined and the last previously determined position, the region to be considered for determining the new position can be larger or smaller.

In one embodiment, when determining the position of the hinge the eye movements performed between the previous and the currently determined position of the hinge or still being carried out, are considered. Particularly, the above-mentioned framework conditions, thus, for example the time, the previous position and/or the eye movements, are combined.

In one embodiment, it can be provided that the determination or detection of the hinge is newly performed for each new image. Alternatively, it can be provided that the hinge is detected a single time prior to the start of the treatment and then the position of the hinge is indicated based on the translatory and rotatory eye movements, for example of the pupil, the iris and/or the limbus.

In one embodiment, it can also be provided to newly determine the position of the hinge only after expiry of a predetermined period of time or after capturing a predetermined number of images and meanwhile to determine the position of the hinge based on the tracked eye movements.

In a further development of the present disclosure, when determining the position of the hinge, the ratio of the areas is considered, in which the straight region—representing the position of the hinge—subdivides the circular region in the manner of a secant. The division ratio reflects the provided hinge-flap geometry which remains equal with the same cutting technique and, in particular, is also independent of the actual size of the flap and the associated hinge. The absolute size of the flap or of the hinge can vary depending on the size of the optical zone of the cornea, with the division ratio remaining about equal, however.

The object is also achieved by a device according to the independent apparatus claim. It relates to a device for determining the position of a flap incision on a cornea and of the hinge associated with the flap, the device comprising a camera for capturing an image of a cornea, an image processing unit for real-time analysis of the image, and a control unit, which is adapted to perform one or all of the afore-mentioned methods. The camera can additionally comprise an illumination unit.

Overall, the method according to the present disclosure and the device according to the present disclosure provide the following advantages:

By avoiding any other instruments touching the eye, the risk of infection is reduced. The treatment result is improved because the position of the flap/hinge is detected and thus only the relevant region is treated.

Imprecise covering of the region by the surgeon by means of the instrument is avoided: because, if too little is covered by means of manual covering, there is a risk of the flap being at least partially ablated. This leads to the postoperative visus being negatively affected. However, if too much is covered—thus also part of the surface to be treated—a region of the optical zone is only insufficiently treated. This also leads to the postoperative visus being negatively affected.

Overall, a smaller number of pulses are needed due to the specifically tailored treatment so that the treatment can be carried out more quickly. Among other things, this reduces the issues involved with the eye drying out during the operation.

Furthermore, the surgeon will be less burdened and can therefore better focus on the procedure and better care for the patient since they no longer need to cover the flap with the aid of an instrument.

When the surgeon's instruments, hand or arm for covering the flap in the conventional manner interfere with the field of view of cameras or the optical path of the illumination, there is a risk that by shadowing the illumination the eye tracking will be compromised or will fail completely. When it is no longer necessary to cover the flap, this risk is eliminated.

BRIEF DESCRIPTION OF THE DRAWINGS

In the following, embodiments of the present disclosure are described as examples with reference to the drawings. In the drawings.

DESCRIPTION OF EMBODIMENTS

Figure 1:
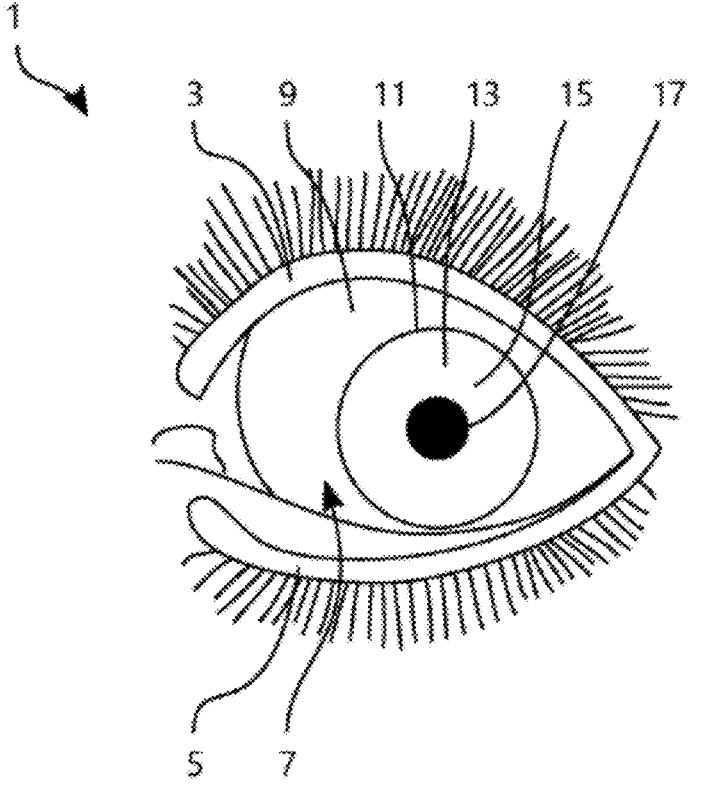
FIG. 1 schematically shows an eye to be treated.

FIG. 1 illustrates, in a schematic representation, an eye 1 to be treated. The illustration of FIG. 1 shows the upper lid 3, the lower lid 5 and the eyeball 7. The sclera 9, the limbus 11 as a transition to the cornea 13, and the iris 15 are schematically shown on the eyeball 7. The pupil 17 is indicated within the iris 15.

Figure 2:
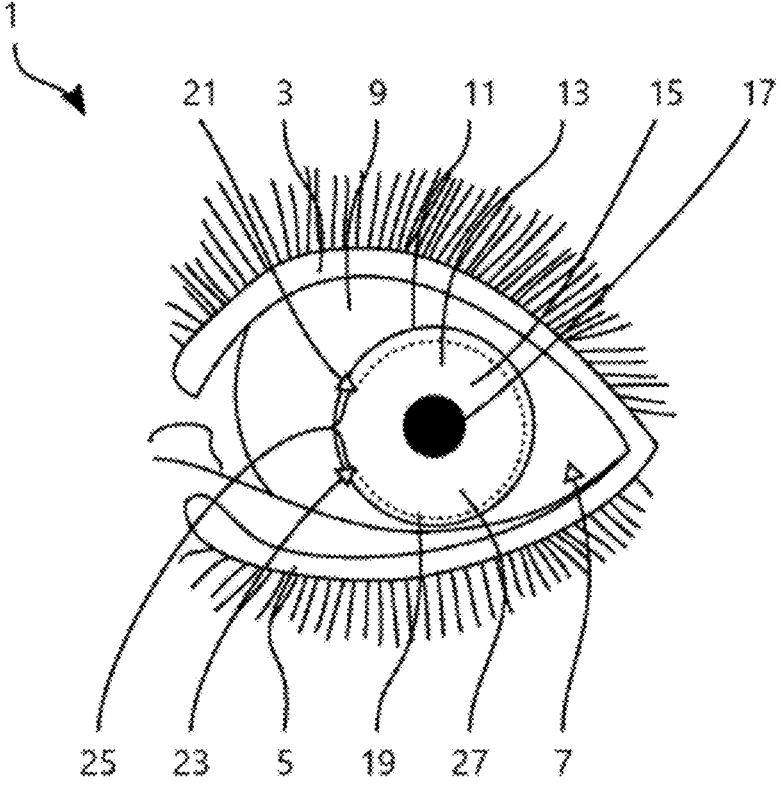
FIG. 2 shows the eye of FIG. 1 with a flap incision indicated as a dash-dot line.

For carrying out a LASIK operation, as initially described, the cornea 13 is incision in an approximately circular shape to gain access to the stroma which is to be reshaped in a subsequent step. The situation after the process of cutting is shown in FIG. 2. The incision can be performed, for example, mechanically by means of a microkeratoma or optically by means of a femtosecond laser. The circumferential line 19 of the incision is indicated as a dashed line in FIG. 2. The incision itself is essentially along a plane of which the normal vector is parallel to the direction of light impingement.

As shown in FIG. 2, the cornea 13 is not fully sectioned, rather, the incision ends at points 21, 23. There is therefore a rest that remains attached to the cornea 13. This rest will later form a kind of joint 25 (a "hinge"), at which the lamella 27 formed by the incision—referred to as a "flap"—can be folded back. This will be described with reference to subsequent FIG. 3.

Figure 3:
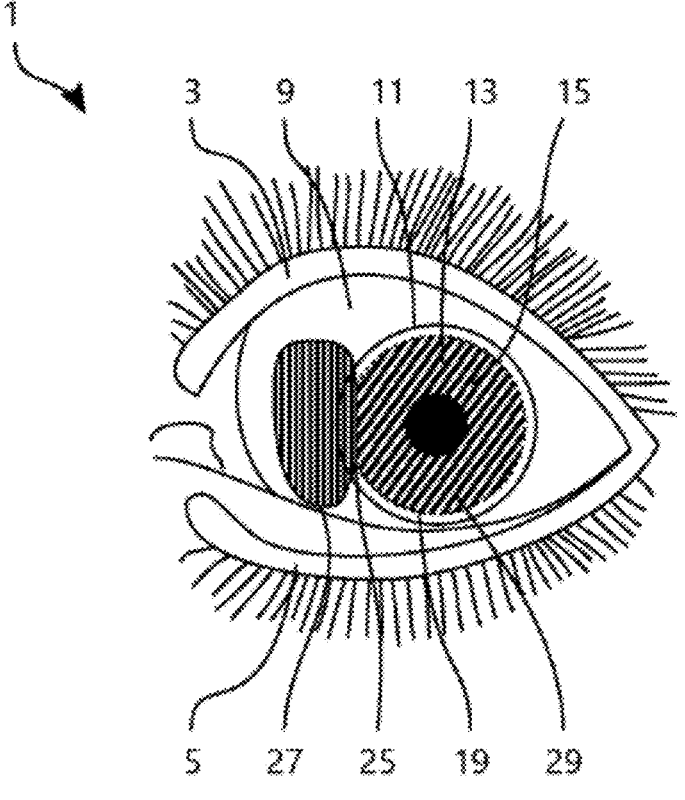
FIG. 3 shows the eye of FIG. 3 with the flap folded back.

FIG. 3 illustrates the state in which the cut-away flap 27 (shown here in cross-hatching) has been folded back. Since, in the example shown, the hinge 25 is nasally situated, the flap 27 will also come to lie in a nasal position. The now openly accessible stroma layer 29 (also shown in cross-hatching) can now be treated.

Both the stroma 29 and the underside of the flap 27 have a reflectivity different to that of the cornea surface. While the outer cornea surface is relatively smooth and has good reflectivity, the stroma surface is relatively dull.

If the flap incision is performed by a microkeratoma or by means of a different laser than the actual ablation laser, the precise position of the flap incision or the exposed stroma 29 is not known during the ablation treatment. The position of the hinge 25 is of particular relevance for the position of the exposed stroma region 29. As already initially mentioned, the position of the hinge can be nasal or superior, for example. The hinge can also have a slightly varying length with the flap incision radius remaining equal, i. e., its position can vary relative to the flap incision center.

To protect the hinge 25 against laser radiation during the ablation process, it is provided according to the present disclosure to detect the position of the hinge 25 based on a camera image and to consider this position during the ablation.

Figure 4:
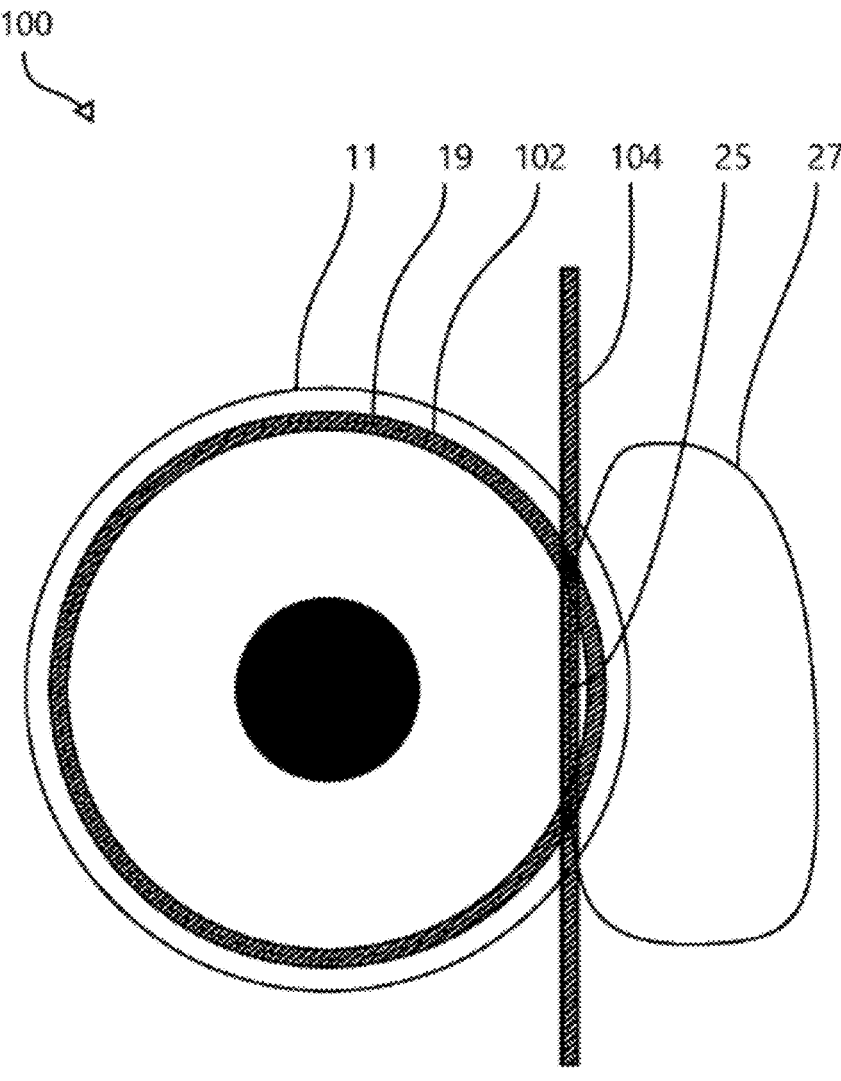
FIG. 4 shows the eye of FIG. 3 including an indicated circular region and a linear region.

FIG. 4 illustrates, in a strongly schematized manner, an image 100 of the eye 1, which at least shows the limbus 11. To keep the representation from being overburdened, in the description of the image of FIG. 4 the structures shown will be given the same reference numerals as the structures themselves.

The method according to the present disclosure for determining the position of the flap incision and of the hinge 25 will be described in the following.

In a first step, in processing the image 100, the position of the outer circumferential line 19 is determined. To reduce computing overhead during this step, it is assumed that the circumferential line 19 is situated in an almost annular region. This is indicated in FIG. 4 by a circular ring 102 in a cross-hatched area. The radial position of the circular ring 102 and the radial extension of the same can be derived from various parameters, such as those that can be derived from the image 100 itself, such as the absolute size of the iris 15, or the limbus 11, or those that can be externally provided to the algorithm, such as information on the way in which the flap 27 was created (microkeratoma/laser), the implements used, or, for example, parameters to be input or determinable by the surgeon.

In a second step, the position of the hinge 25 is determined by means of a linear region 104. This linear region 104 is also used at first to limit the possible image regions to be processed. The position of the linear region, just like the position of the circular region 102 before, can be made dependent on parameters, such as the preferred positioning of the hinge 25, the way in which the hinge 25 was created, or other parameters, such as can be or must be input by the surgeon.

The position and extension of the linear region 104 can be determined independently from the previous determination of the circular region 102 or of the outer circumferential line 19 of the flap incision. It may, however, be preferred if the determination of the position and/or the extension of the linear region 104 is determined in dependence on the determination of the outer circumferential line 19. For example, the ratio with which the hinge position subdivides the circle defined by the outer circumferential line 19, can be used as a criterion. This is shown in the subsequently described FIG. 5.

Figure 5:
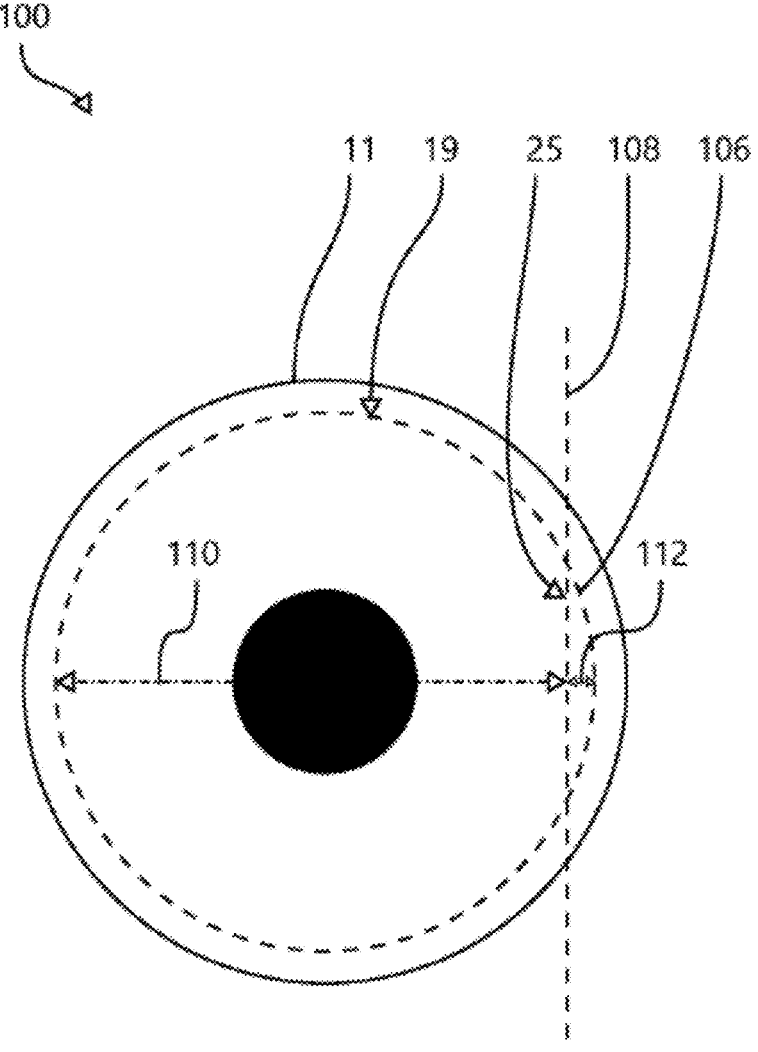
FIG. 5 shows the eye of FIG. 4, including a detected circular incision line and a linear hinge line.

FIG. 5 illustrates, in a strongly schematized manner, the result of the determination of the position of the outer circumferential line and of the hinge of a flap incision. In FIG. 5, as a result of the determination of the outer circumferential line 19 a dashed circular line 106 is indicated. Furthermore, as a result of the determination of the position of the hinge 25, a dashed straight line 108 is indicated. As already mentioned, in determining the position of this straight line 108, the above-mentioned division ratio can be considered. This is illustrated in FIG. 5 by the distances 110, 112 provided with arrows at either end. For the computation of the division ratio, as shown in FIG. 5, the length of the two distances 110, 112 or the surface areas of the areas crossed by the two distances 110, 112 can be used.

For computing the length of the hinge 25 and thus, among other things, the position of the straight line 108, apart from the criteria mentioned above, further criteria can be used to improve the computation result and to reduce the computational overhead.

In the current determination of the position of the hinge 25, it can be considered that the position currently to be determined of the hinge 25 can only deviate from the previously determined position of the hinge 25 within certain limits. The limits can be determined, for example, based on the time elapsed since the previous determination of the position of the hinge 25. Further parameters to be included in the computation can be, for example, the eye movements having occurred and/or occurring between the time point of the last determination of the position of the hinge 25 and the current point in time.

Furthermore, it can be considered that with certain surgical techniques or/and surgeons the hinge 25 always has a certain orientation (nasal, superior etc.) or has a certain division ratio.

Figure 6:
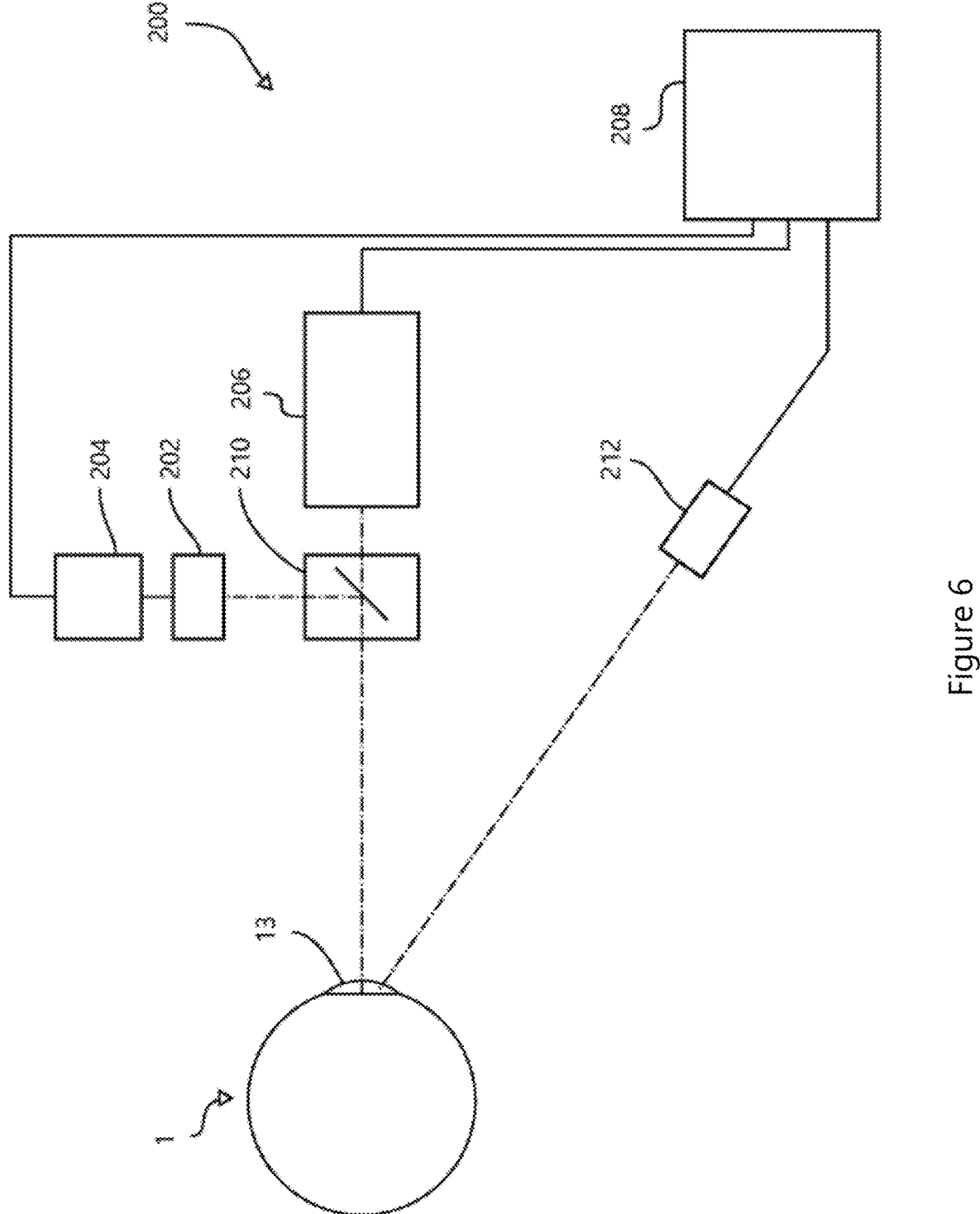
FIG. 6 shows, in strongly schematized fashion, a device suitable for carrying out the method.

FIG. 6 illustrates, in a strongly schematized manner, a device 200 for determining the position of a flap incision on a cornea 13 of an eye 1 and of the hinge 25 associated with the flap. The device 200 comprises a camera 202 for capturing an image 100, as shown, for example, in the FIGS. 4 and 5 as described above. The camera 202 is integrated into the axial optical path of the treatment unit 206—for example a treatment laser by means of a beam divider 210. The treatment unit 206 can be adapted, for example, to carry out a LASIK or similar operation on the eye 1.

The camera 202 can also be supplemented by an illumination unit 212, which can provide homogeneous illumination and/or can project patterns helping with the detection, such as stripes, onto the cornea. It can be advantageous, for example, for the orientation of the stripes to be perpendicular to an expected orientation of the hinge 25. The illumination patterns can lead to better detectability of the circular incision and of the hinge 25. In an embodiment, an illumination wavelength in the IR range is used to provide independence from the illumination settings used for the visual control carried out by the surgeon.

The device 200 further comprises an image processing unit 204, which is schematically shown as separate from the camera 202 in FIG. 6. However, this separation only serves to illustrate the functionality. From a structural point of view, the image processing unit 204 could also be integrated in the camera 202 or be part of a larger data processing unit, such as a computer. The image processing unit 204 is adapted to process in real time an image 100 produced by the camera 202. This means that the images provided by the camera 202 in the necessary speed can be processed and evaluated without delay.

Both the image processing unit 204 and the treatment unit 206 are connected to a control unit 208. The control unit 208 can receive the evaluation parameters provided by the image processing unit 204, such as the position of the outer circumferential line 19 and/or of the hinge 25. At the same time, the control unit 208 is further adapted to control the treatment unit 206 by means of the evaluation parameters of the image processing unit 204. For example, the control unit 208 can delimit the region to be ablated in a LASIK treatment based on the evaluation parameters in such a manner that the hinge 25 is not ablated.

What is claimed is:

1. A method for determining a position of a flap incision, after the flap incision has been formed, on a cornea and a position of a hinge associated with a flap produced by the flap incision, the method comprising the steps of:
   a) capturing an image of an eye, which at least includes a pupil, a limbus, and the flap;
   b) determining, by a processor, a region including an outer circumference of the flap incision; and
   c) determining the position of the flap incision; and/or
   d) determining a straight region comprising the hinge; and
   e) determining the position of the hinge.

2. The method according to claim 1, wherein the step (b) of determining a region including the outer circumference of the flap incision comprises:
   determining an approximately circular region as a region including the outer circumference of the flap incision.

3. The method according to claim 2, wherein the step (d) of determining a straight region comprising the hinge comprises:
   delimiting a possible position of the straight region to a region within the circular region.

4. The method according to claim 1, wherein the step (e) of determining the position of the hinge comprises:

comparing a currently determined position to a previous position of the hinge.

5. The method according to claim 4, wherein, in determining the position of the hinge, an elapsed time is considered and that has elapsed between the previous position and the currently determined position of the hinge.

6. The method according to claim 1, wherein, in determining the position of the hinge and/or of the flap incision, eye movements that have occurred between the previous position and the currently determined position are considered.

7. The method according to claim 4, wherein, in determining the position of the hinge, a ratio of surface areas is considered into which the straight region divides the circular region in a form of a secant.

8. A device for determining the position of the flap incision on the cornea and the position of the hinge associated with the flap, the device comprising:
   a) a camera for capturing the image of the cornea;
   b) an image processing unit for real-time analysis of the image, and
   c) a control unit configured to carry out the method according to claim 1.

9. A method for determining a position of a flap incision on a cornea and a position of a hinge associated with a flap produced by the flap incision, the method comprising the steps of:
   a) cutting the flap incision, which produces the flap and the hinge, on the cornea;
   b) capturing an image of an eye, which at least includes a pupil, a limbus, and the flap;
   c) determining, by a processor, a region including an outer circumference of the flap incision; and
   d) determining the position of the flap incision; and/or
   e) determining a straight region comprising the hinge; and
   f) determining the position of the hinge.

* * * * *